United States Patent [19]

Prior et al.

[11] Patent Number: 4,501,143
[45] Date of Patent: Feb. 26, 1985

[54] PREPARATION UNIT FOR A DRILLING MUD TESTING SYSTEM

[75] Inventors: Maurice Prior, Duncanville; M. Scott Quigley, Garland, both of Tex.

[73] Assignee: Mobil Oil Corporation, New York, N.Y.

[21] Appl. No.: 518,569

[22] Filed: Jul. 29, 1983

[51] Int. Cl.³ .............................................. G01N 33/24
[52] U.S. Cl. .......................................... 73/153; 73/53
[58] Field of Search ...................... 73/153, 61.4, 64.1, 73/53; 374/45

[56] References Cited

U.S. PATENT DOCUMENTS 3,473,368  10/1969  Roper ............................ 73/61.4 X
4,304,122  12/1981  Tentor ............................ 73/153 X Primary Examiner—Jerry W. Myracle
Attorney, Agent, or Firm—Alexander J. McKillop; Michael G. Gilman; Charles J. Speciale

[57] ABSTRACT

In a system for testing drilling mud, a mixing tank and an aging vessel are hydraulically connected to supply drilling mud to a closed recirculating path through which mud is pumped to measuring instrumentation. The accumulator has a head which is removable for inspection and maintenance of the gas pressurized piston which pressurizes the drilling mud. The seals on the head are positioned to minimize wear.

6 Claims, 12 Drawing Figures

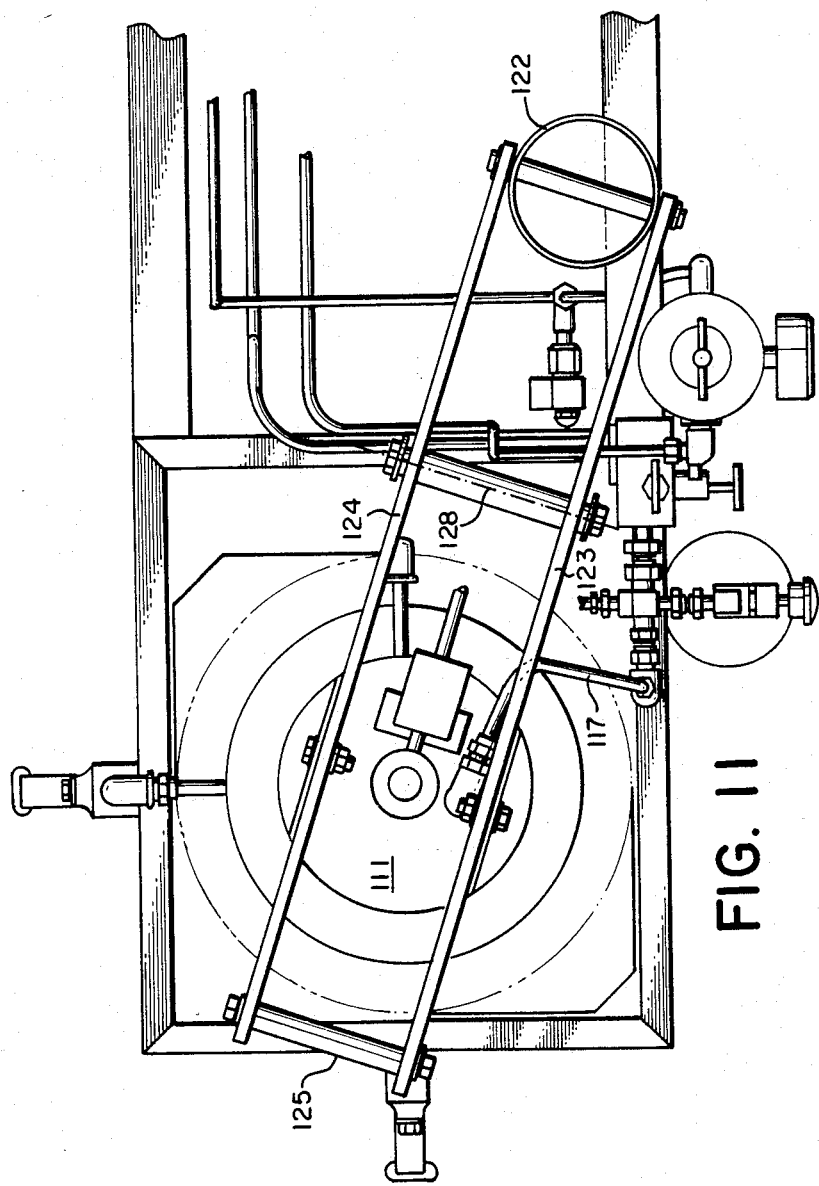

PREPARATION UNIT FOR A DRILLING MUD TESTING SYSTEM

BACKGROUND OF THE INVENTION

This invention relates to a system for testing the parameters of drilling mud, and more particularly, to a unit for preparing the drilling mud to be tested.

In the drilling of wells, such as oil or gas wells, by the rotary method, a drilling mud is circulated from the surface of the earth to the drill bit and back to the surface again for the purposes of cooling the drill bit, removing earth cuttings from the bore hole, and imposing a hydrostatic pressure on the drilled earth formations to prevent flow of fluid therefrom into the well bore hole. In a drilling mud containing water and clay, the rheological properties of plastic viscosity, gel strength, and yield point, which must be maintained within limits in order that the drilling fluid remain pumpable and perform its desired functions, depend largely upon the concentration of clay solids and the extent to which the clay solids are hydrated by and dispersed within the water contained in the fluid.

Drilling muds are used under a wide variety of conditions which require that different compositions be used. For example, where the well bore hole passes through formations containing clay, the clay admixes with the drilling mud and this clay is hydrated by and dispersed by the water in the drilling fluid, thereby increasing the concentration of dispersed clay solids. The increase in the concentration of dispersed clay solids deleteriously affects the rheological properties of the drilling mud. Accordingly, where control of rheological properties is important, the drilling mud should have a minimum change in such properties with increasing concentrations of clay solids.

Usually, drilling muds are shear thinning, i.e., they increase in viscosity at low shear rates and decrease in viscosity at high shear rates, whereby the cuttings may be readily separated from the drilling fluid at the surface of the earth and, in the event circulation of drilling fluid is stopped for any reason, the cuttings will be properly suspended by the drilling fluid within the well and not sink to the bottom thereof with resultant danger of sticking drill pipe. The rheological properites of a drilling mud are ordinarily imparted thereto by virtue of employing a clay such as bentonite as one of the constituents. Since one of the functions of a drilling mud is to impose a hydrostatic pressure on the formations penetrated by the well, it is desirable that the drilling mud have the appropriate density, and density of a drilling mud is increased by adding a weighting agent such as barite. Drilling muds also often contain caustic soda which is added to solubilize certain constituents, inhibit fermentation of organic additives, reduce the effect of contaminants picked up during drilling and to affect other results depending on the type of drilling mud being employed.

Another property desired in a drilling mud is that of resisting gelation at high temperature. With increasing depth of the well, the bottom hole temperature increases. In many wells, these temperatures exceed 300° F. With aqueous drilling muds, high temperatures induce cementation reactions between clay minerals and various drilling mud additives. As a result, the drilling mud tends to attain excessively high gel strengths. With gelation, excessively high pump pressures are required to break circulation with the result that often loss of the drilling mud occurs by being forced into permeable formations. Additionally, gelation of the drilling mud can prevent logging tools from reaching the bottom of the well.

Frequently, during the drilling of a well, drilling conditions change. Changes in temperature occur. The character of the formations being drilled may change, as for example, salt may be encountered. Each change in drilling conditions can affect the properties of the drilling mud. Frequently, to counteract the effect of the changed drilling conditions on the properties of the drilling mud, a change in the composition or character of the drilling mud is required.

The foregoing and other considerations dictate that drilling muds be tested under conditions which closely approximate conditions which would be encountered during drilling. By adding different additives, and by subjecting the drilling mud to various conditions of temperature and pressure, a determination can be made as to whether the mud will perform adequately under actual drilling conditions.

Prior art systems for testing drilling muds have the disadvantage of occasional spillage of drilling mud with its attendant inconvenience. The prior art drilling mud testing system, on which the present invention is an improvement, has an accumulator which pressurizes the drilling mud and valves that prevent leakage of pressurized mud into the laboratory where the testing system is operated. If these valves are not properly operated, pressurized drilling mud escapes into the laboratory. Further, in the prior art system drilling mud must be manually transported from the vessel in which it is mixed to the system where it is tested. This also provokes mud spillage. The mud accumulator in this prior system also has the disadvantage that the piston seals are exposed to the mud and subject to increased wear because of this exposure. Furthermore, the seals are not readily accessible for cleaning and/or replacement.

It is an object of the present invention to provide a drilling mud testing system with improved protection against mud spillage.

It is another object of the present invention to provide a drilling mud testing system having an accumulator with improved access to the piston for inspection and routine maintenance.

RELATED APPLICATIONS

The following related applications are incorporated herein by reference: Ser. No. 518,336, filed July 29, 1983, "FLUSHING APPARATUS FOR A DRILLING MUD TESTING SYSTEM", Ser. No. 518,568, filed July 28, 1983, "CONTROLLED HEATER FOR DRILLING MUD TESTING SYSTEM", Quigley and Russell and Ser. No. 518,565, filed July 29, 1983, "DRILLING MUD TESTING SYSTEM HAVING A THERMALLY ISOLATED PUMP".

SUMMARY OF THE INVENTION

In accordance with the present invention, a system for testing drilling mud includes an accumulator for pressurizing the drilling mud and a closed recirculating path in which pressurized drilling mud is pumped through measuring instrumentation. A mixing vessel in which mud to be tested is mixed and an aging vessel in which the mud is conditioned are hydraulically connected to the accumulator so that the mud to be tested can be delivered to the closed recirculating path without spillage.

The accumulator has a nitrogen driven piston which pressurizes the drilling mud. In accordance with the invention, the accumulator has a removable top which is counter-balanced so that it can be easily positioned on the accumulator vessel and removed therefrom for inspection of the piston seals and maintenance thereof.

During operation, the mud circulates in the closed path which is not easily accessible. Barring deliberate intervention, the system is protected from accidental spillage of the mud.

The foregoing, and other objects, features and advantages of the invention will be better understood from the following more detailed description and appended claims.

SHORT DESCRIPTION OF THE DRAWINGS

FIG. 1A shows the manner in which FIGS. 2-9 fit together to show the details of the drilling mud testing system of the present invention;

FIG. 11 is a top view of the accumulator.

DESCRIPTION OF THE PREFERRED EMBODIMENT

Figure 1:
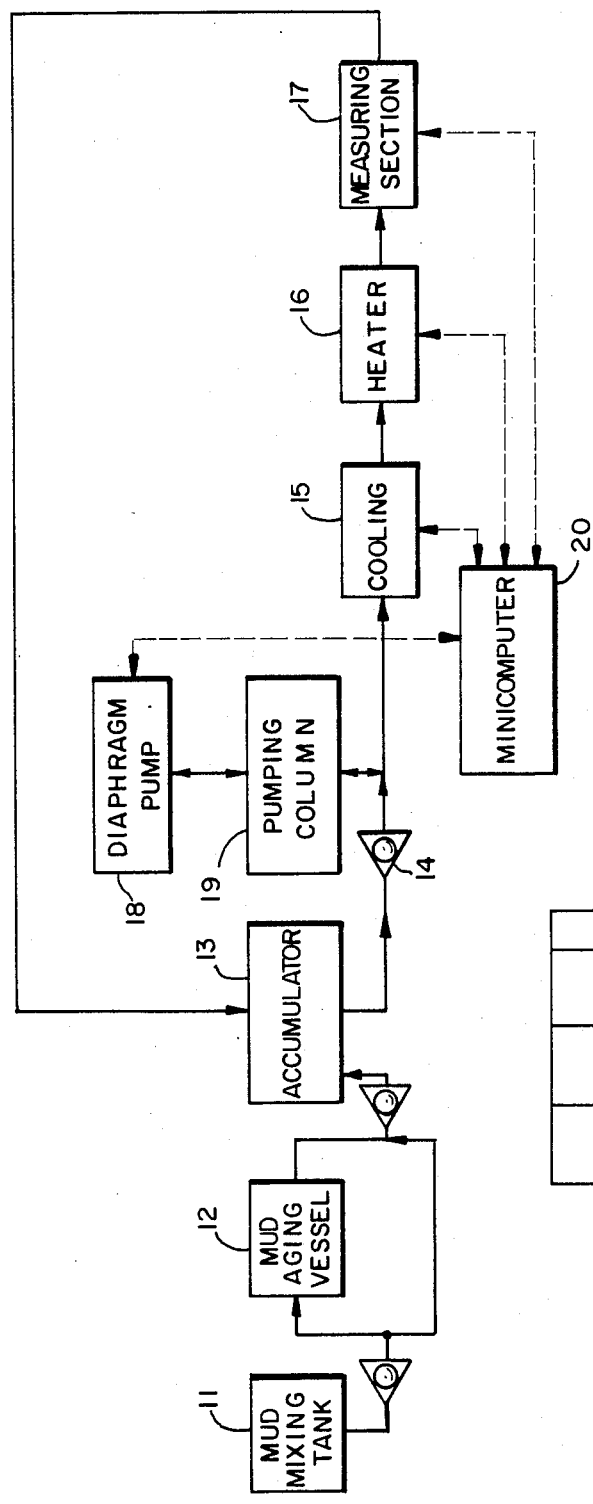
FIG. 1 shows the drilling mud testing system of the present invention.

Referring to FIG. 1, the system for testing drilling mud includes an open mixing tank 11 for mixing muds and additives, and an aging vessel 12 for aging the mud at high temperature and under pressure. An accumulator 13 pressurizes the drilling mud so that it circulates at the desired pressure.

Mud travels in the closed recirculating loop which includes check valve 14, cooling heat exchanger 15 and heater 16 which heats the drilling mud to an elevated temperature. The parameters of the mud are measured in the measuring section 17.

The mud is pumped in the closed loop by the diaphragm pump 18. In accordance with the present invention, mud from mixing tank 11 and/or aging vessel 12 can be hydraulically supplied to the accumulator 13 without risk of spillage. Further in accordance with the present invention, the only access to the mud in the recirculating path is through the accumulator 13 which has a removable top. This permits access to the seals in the accumulator for inspection and maintenance. However, the top of the accumulator cannot be removed when the closed loop is pressurized, and this prevents accidental spillage.

The mud is pumped in the closed loop under control of minicomputer 20 which receives inputs indicating mud temperature, pressure, and other parameters, and produces control signals controlling the operation of the system.

Figure 8:
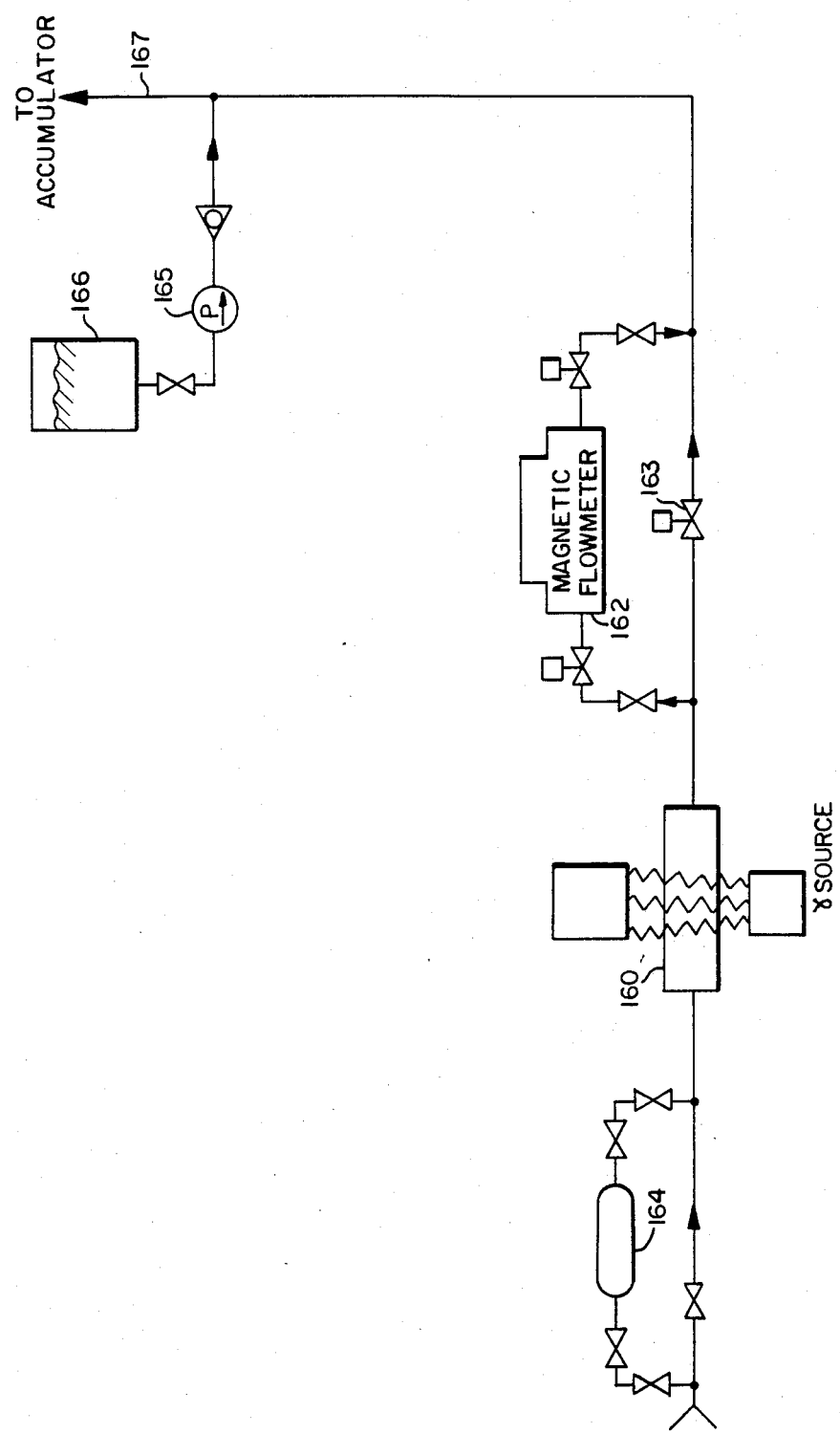
Figure 9:
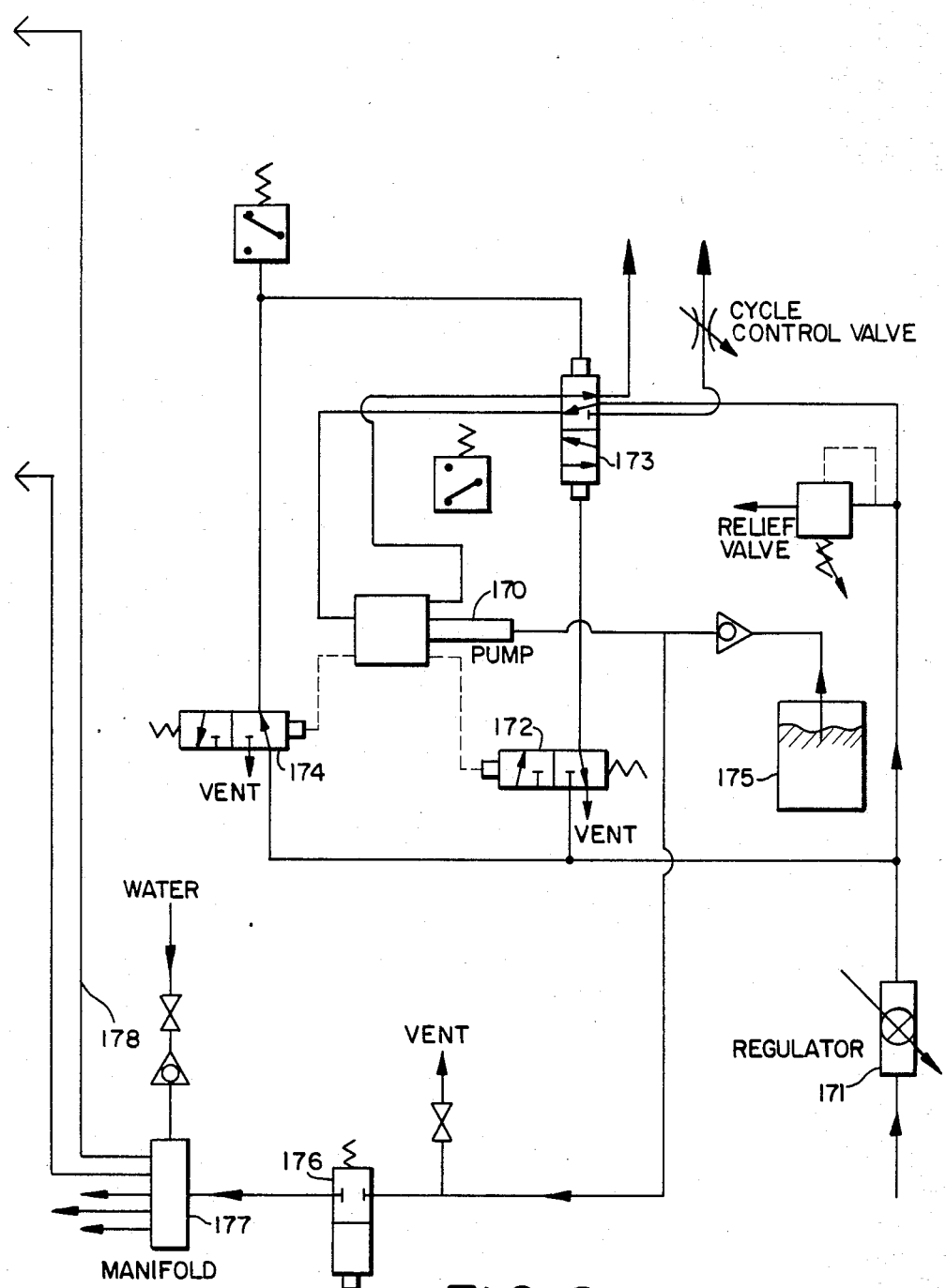
Figure 10:
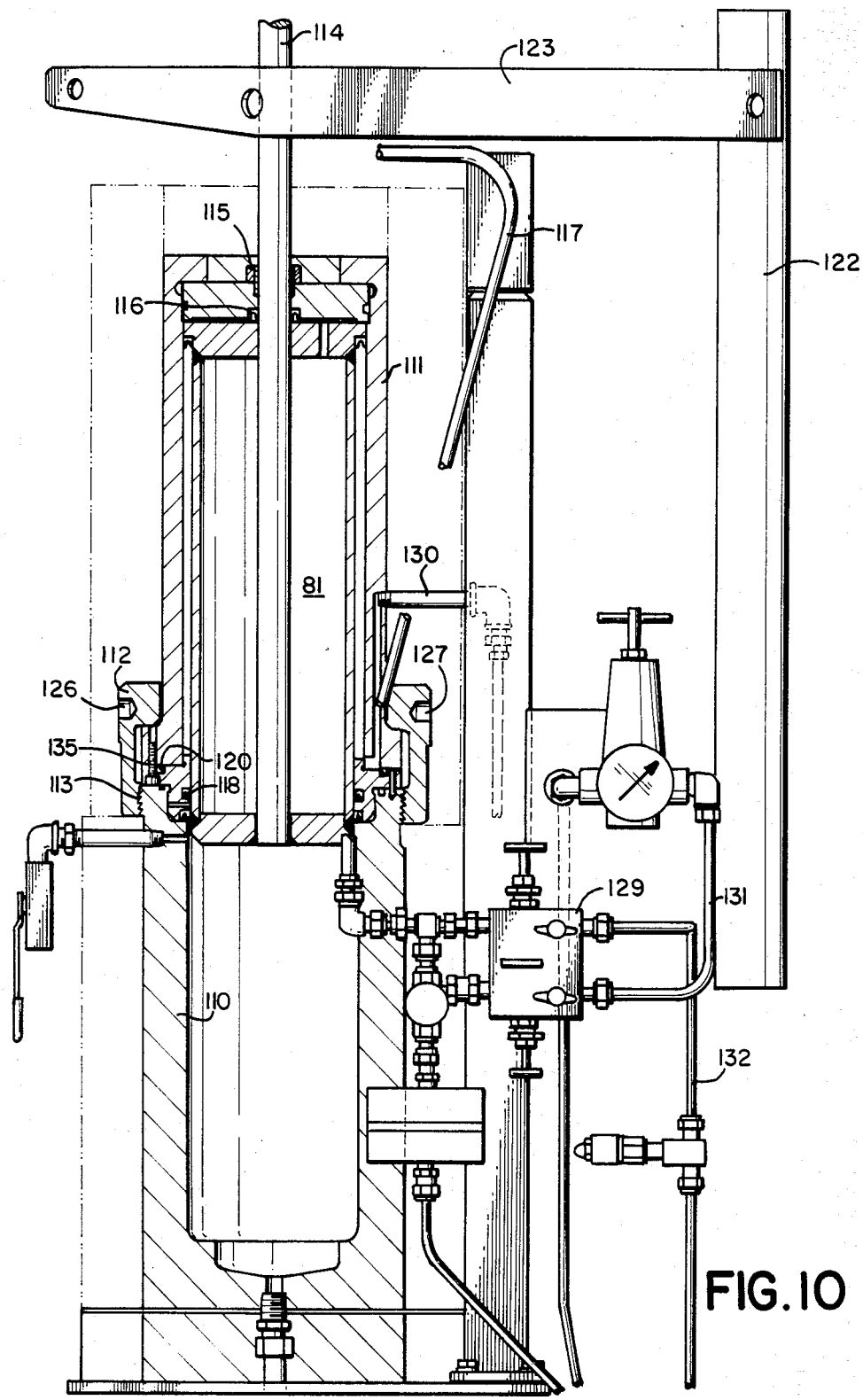
FIG. 10 is a side elevation view of the accumulator.

The foregoing will be better understood from reference to FIGS. 2-9 which show the various components of the system, and by reference to FIGS. 10 and 11 which show the accumulator in more detail.

Figure 2:
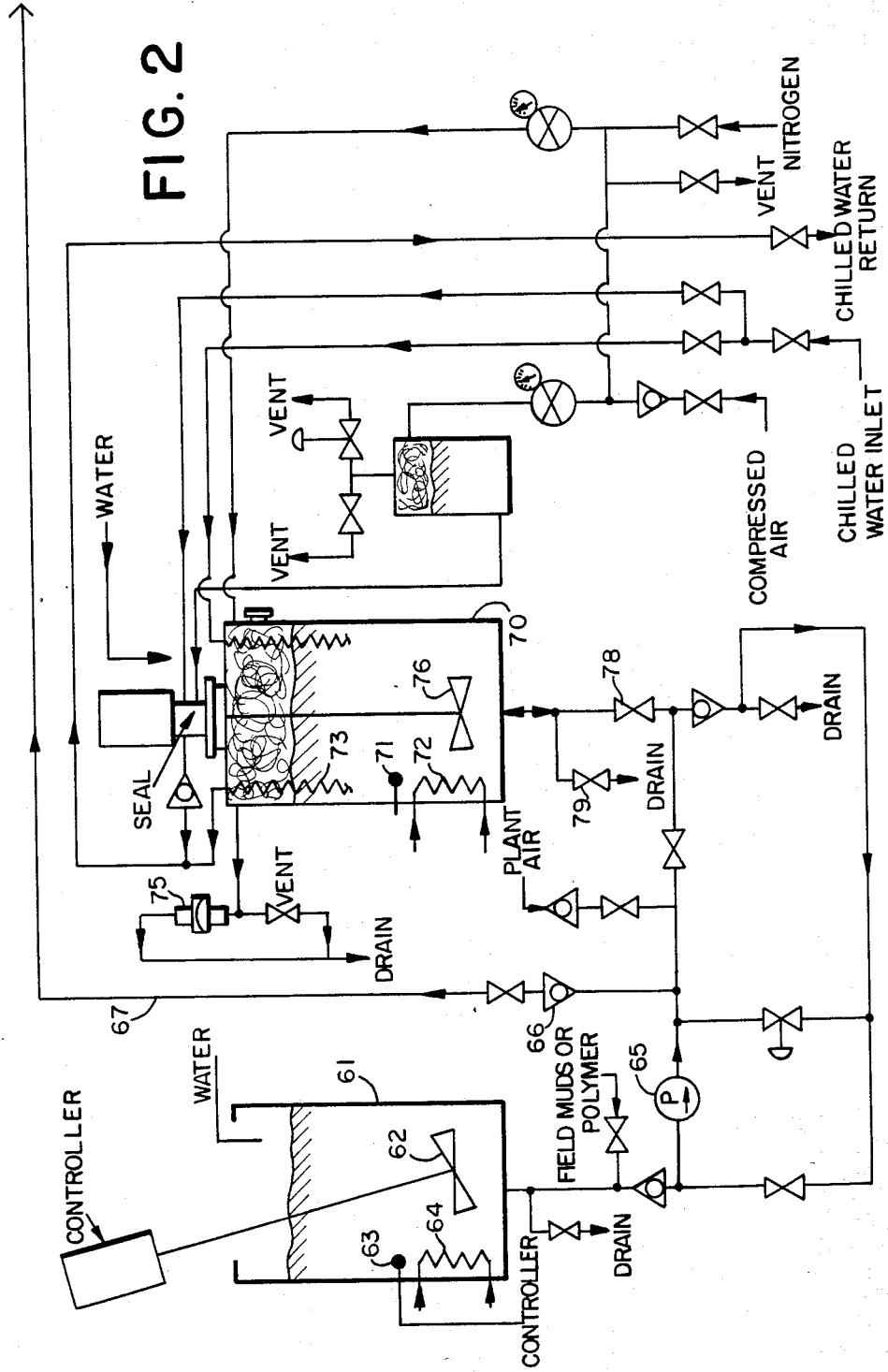

FIG. 2 shows the mud preparation section of the system where the drilling mud is mixed and aged. Open mixing tank 61 is, for example, a tank of approximately 6 gallon capacity, which has a mixing paddle 62 for mixing drilling muds. Thermocouple 63 is connected to the mixing heater controller which, in turn, controls the heater 64. Transfer pump 65 is used to transfer mud directly into the system through check valve 66 and thence to the main loop 67. Alternatively, pump 65 transfers mud from mixing tank 61 to the aging vessel 70.

Aging vessel 70 is approximately a 6 gallon vessel. It maintains the mud at approximately 350° F. and under a pressure of 150 psi maximum. Thermocouple 71 is connected to the controller which in turn controls heater 72. Aging vessel 70 also includes cooling coil 73. Mixer 76 is provided to shear the mud and homogenize it. The mud is maintained under pressure in aging vessel 70 so that it does not boil at the aging temperature. When the mud has been properly aged, chilled water is supplied to the cooling coil 73 to the cool the mud to the proper temperature. Mud is withdrawn from the aging vessel 70 through a screen in the bottom of the vessel, through valve 78 to the suction side of pump 65. Pump 65 pumps the mud through check valve 66 to the main loop 67.

A transfer pump is arranged in conjunction with the valves so that mud can be transferred only from the mixing tank to the aging vessel or to the main loop 67 of the system. Valving is also provided so that mud can be transferred from the aging vessel 70 only to the main loop of the system. Because of this, hot mud from the aging vessel can never be transferred to the open mixing tank 61. Once the mud is in the aging vessel 70, it can be discharged through valve 79 to drain, or it can be transferred to the main system. This is an important feature which prevents accidental spillage of hot mud which is quite undesirable.

Figure 3:
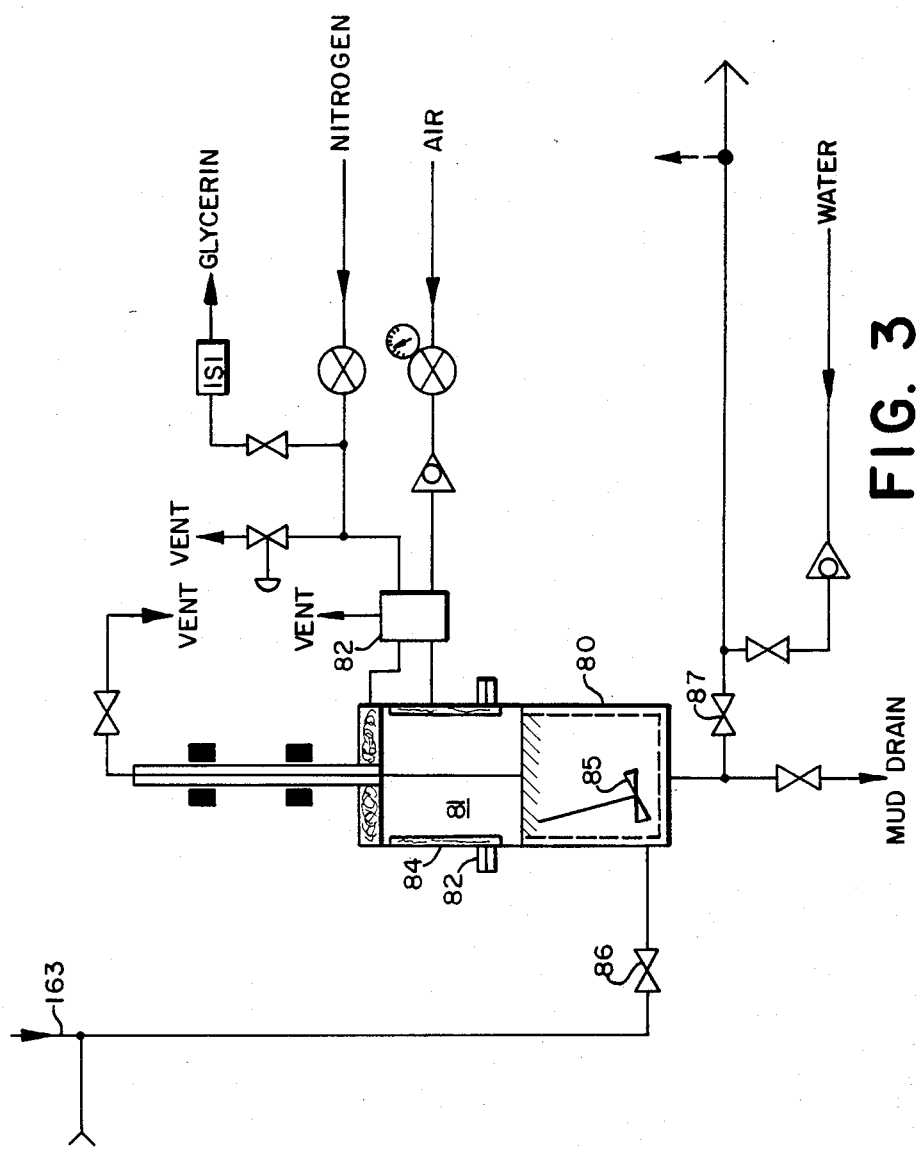

FIG. 3 shows the accumulator 80 which is used to pressurize the mud to 1500 psig maximum. A piston 81 in the top of the accumulator is driven by pressurized air or nitrogen supplied through a manifold valve. Accumulator 80 has a removable head to permit access to it. Flange 82 provides access to the accumulator.

When the system is to be pressurized, the head 84, including the piston, is moved on its counter-balanced suspension to place it over the accumulator 80. The threads of the flange 82 are tightened. Then, nitrogen gas pressure applied to the top side of the piston 81 pressurizes the mud, but at no time does gas reach the mud. This is important to prevent forcing gas into the mud.

The head of the accumulator is removable so that periodic inspection can be made of rings and the like to ensure that gas is not escaping into the mud. The seal on the accumulator ensures that the flange cannot be unlocked when the accumulator is under pressure, thereby preventing accidental mud spillage. Also, the removable head permits changes in the mud composition at reduced temperature and pressure during an experiment.

After the mud has been cooled to approximately 180° F., the flange 82 can be unlocked and the head can be removed. This allows addition of solid or liquid additives to the mud which is being tested. A portable mixer 85 in a wire basket can be inserted into the accumulator to provide proper mixing and then removed prior to replacing the head and operating the system.

When the head 84 of the accumulator is removed, the piston 81 can be driven downwardly by air so that the operator can inspect the piston for wear. The piston can then be driven back up into the head by air.

During operation, the mud flows into the accumulator through valve 86. It flows out of the accumulator through valve 87 to the suction side of the pump. The accumulator provides mud under a constant pressure to the pump.

Figure 4:
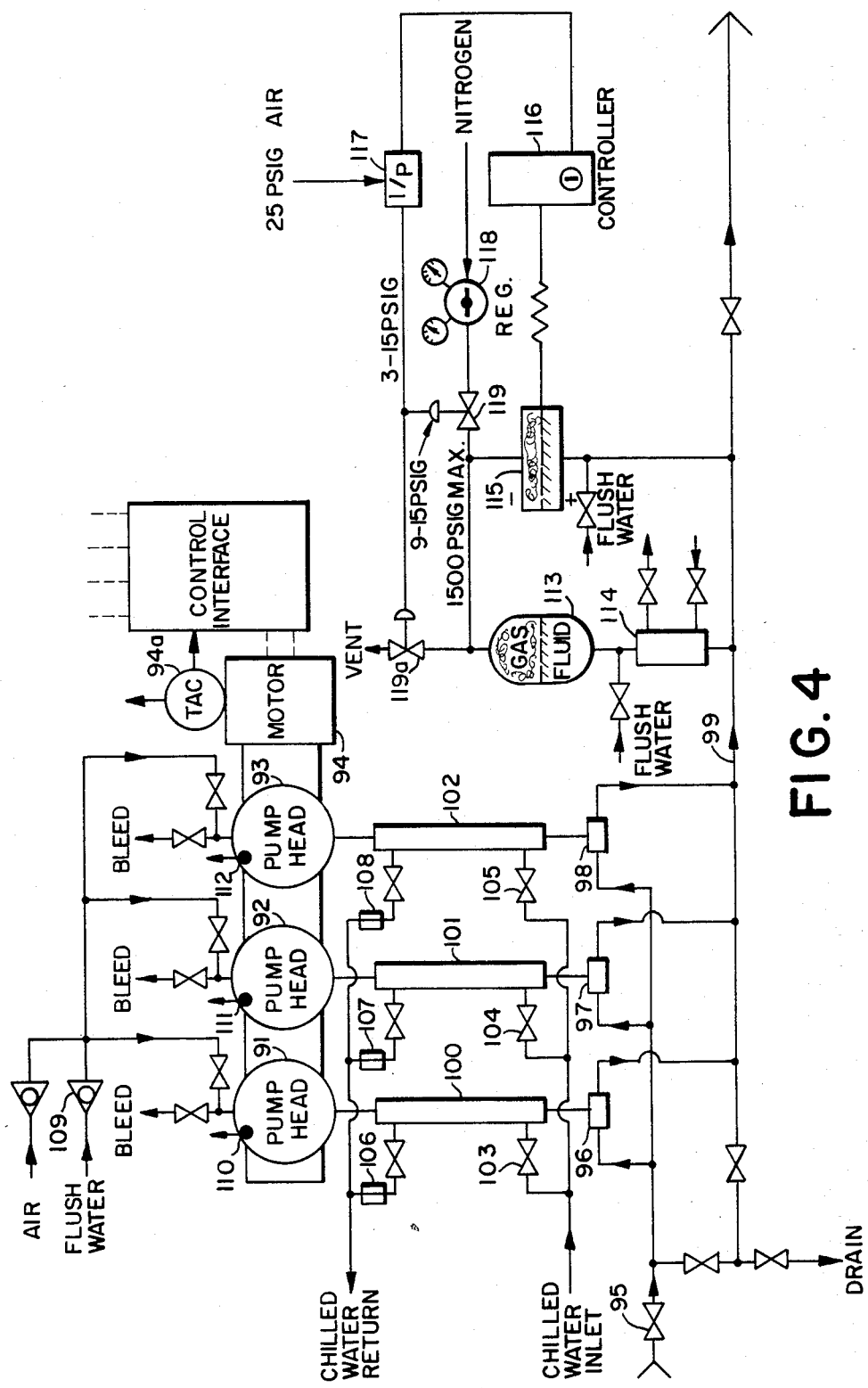

FIG. 4 shows the pump which includes pump heads 91, 92, and 93 driven by a common motor 94. The pump and the intervening pumping column are the invention claimed in "DRILLING MUD TESTING SYSTEM HAVING A THERMALLY ISOLATED PUMP," Prior, Ser. No. 518,565, filed July 29, 1983. The mud flow path is through valve 95 and through the double ball check valves 96-98. The line 99 leads to the cooling and heating section. On successive strokes of the diaphragm in each of the pump heads 91-93, mud is withdrawn from the flow path and discharged into the flow path through the check valves 96-98. There is a water cooled pumping column between pump head 91 and check valve 96, between pump head 92 and check valve 97, and between pump head 93 and check valve 98. Specifically, heat exchangers 100-102 contain a column of drilling mud which thermally isolates the heat sensitive diaphragms of the pumps 91-93 from the heated drilling mud in the flow path. Chilled water is supplied through valves 103-105 to the heat exchangers.

Flush water is supplied through check valve 109 to flush the diaphragms in the pump heads.

Thermocouples 110-112 detect any over temperature caused by the excursion of hot mud into the pump heads and operate an alarm which prevents damage to the diaphragms under this malfunction condition.

Pumps 91-93 are positive displacement diaphragm pumps which have diaphragms of an elastic material which will tolerate only 300° F. Since the circulating mud can be 500° F., these diaphragms must be protected from over temperature.

In order to dampen pulsations in the flow path 99, a pulsation dampener 113 is provided. It is connected through heat exchanger 114 to the flow path 99. The pulsation dampener 113 has a controllable pressure gas head. Transducer 115 senses the pressure differential between the flow path 99 and the gas head in pulsation dampener 113. The flow pulsations caused by the pumps 91-93 are dampened out by the pulsation dampener 113 when the correct pressure differential is maintained. The controller 116 provides electrical signals to the current/pressure transducer 117 which in turn supplies air pressure signals to the control valves 119 and 119a. These control valves alternately open and close as required to maintain the correct pressure differential between the flow path 99 and the gas head in pulsation dampener 113. The desired pressure differential is set on controller 116. Nitrogen gas pressure is supplied to the pulsation dampener gas head 113 via the regulator 118 and control valve 119. Control valve 119a is used to vent excess nitrogen gas.

Figure 5:
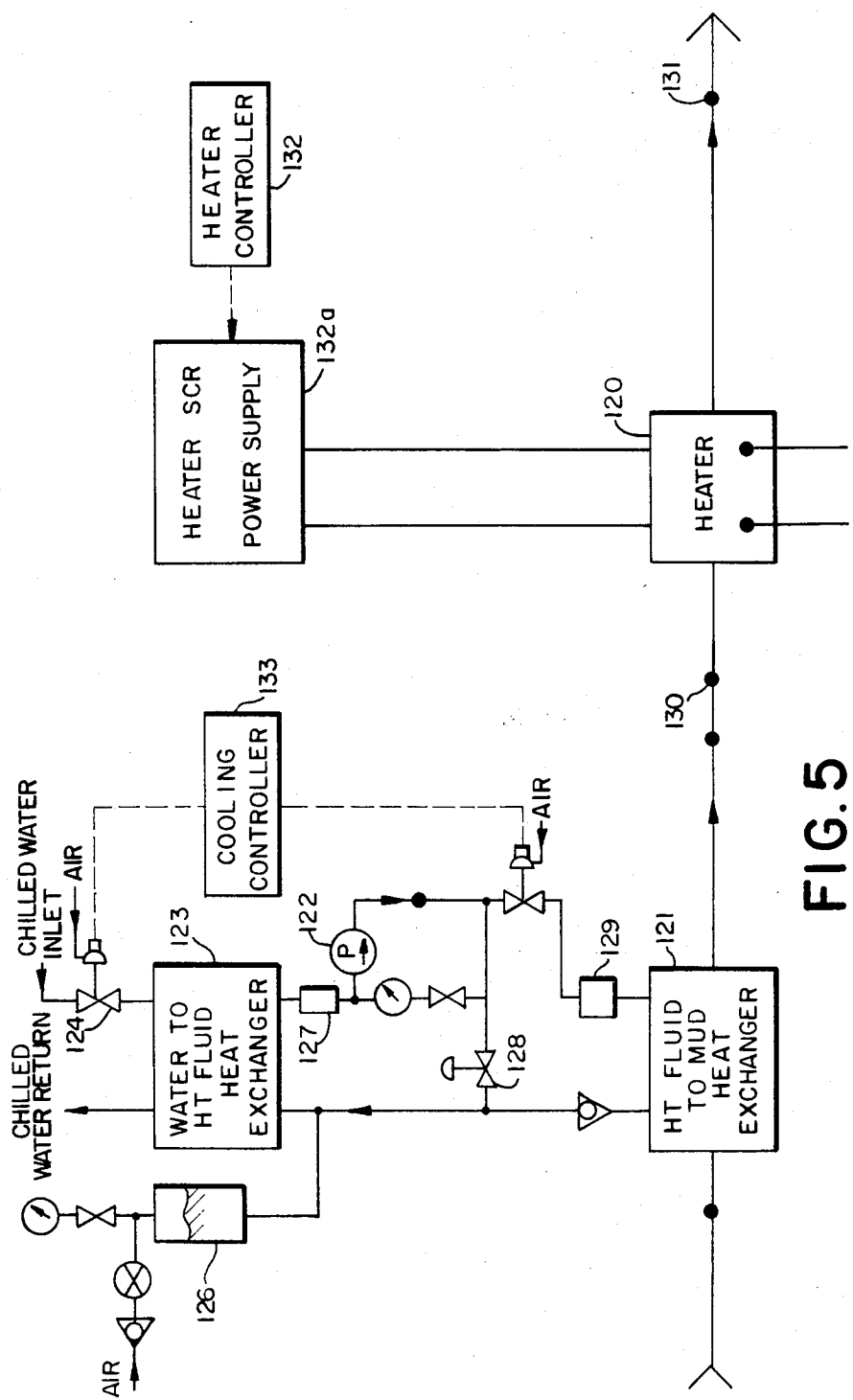

The heat exchange section is shown in FIG. 5. It includes heater 120 which is the invention disclosed and claimed in application Ser. No. 518,568, filed July 29, 1983, "CONTROLLED HEATER FOR DRILLING MUD TESTING SYSTEM", Quigley and Russell. The system is arranged to maintain an approximately constant temperature increment across the heater 120. In order to provide rapid heating of the drilling mud initially, a large capacity heater is required. Such a large capacity heater cannot be used to efficiently control the temperature of the drilling mud after it has reached the desired temperature. This requires small changes in temperature when the system is operating, which would require turning heater elements on and off. In order to avoid this, the mud is first cooled in a heat exchanger 121 before it enters the heater. The cooling is relatively small, for example, from approximately 400° F. to 375° F. The heater 120 supplies a constant amount of heat to the slightly cooled mud.

A heat transfer fluid such as silicon oil, is the heat exchange medium in heat exchanger 121. Pump 122 circulates the heat transfer fluid between the heat exchanger 121 and the heat exchanger 123. Chilled water is supplied to heat exchanger 123 through the control valve 124. A reservoir 126 contains the heat transfer fluid.

Flow switch 127 is activated when the system is flowing properly. A back pressure regulator 128 and a flow meter 129 are provided to ensure proper flow of heat exchanger fluid through the heat exchanger 121.

Thermocouples 130 and 131 sense the temperature at the inlet and the outlet of heater 120. Heater controller 132 controls the heater power supply 132a to bring the mud temperature up to its desired level, for example, 400° F.

Thereafter, cooling controller 133 controls the cooling of the mud to maintain the temperature differential across the heater 120 at a constant value. For example, if a differential of 25° F. is to be maintained, the mud is cooled by heat exchanger 121 to approximately 375° F. so that this temperature differential can be maintained across the heater 120.

Figure 6:
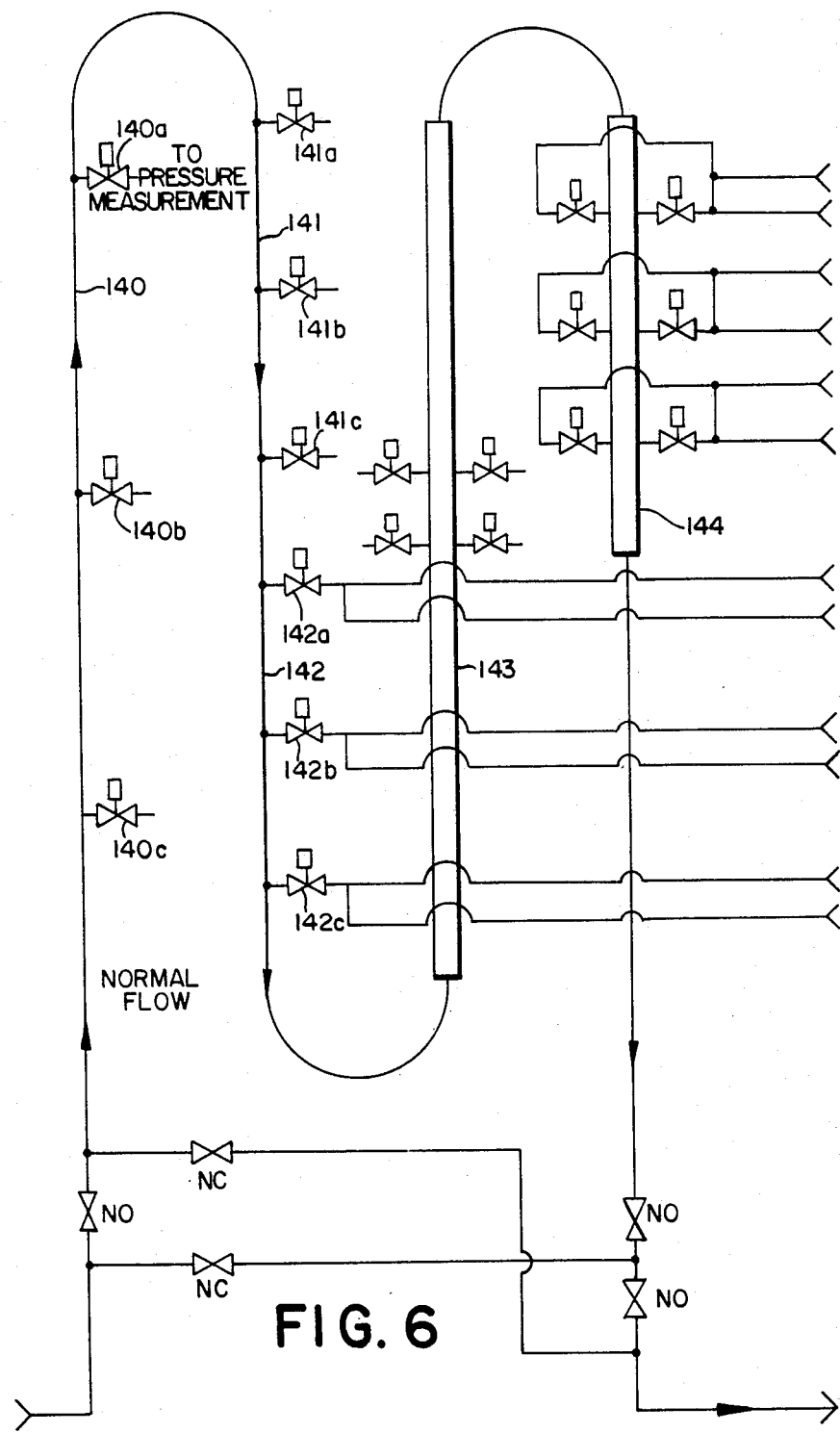

Referring to FIG. 6, the measuring section for testing the parameters of the drilling mud includes viscosity measuring tubes 140-144. Each viscosity measuring tube has three pressure measuring taps. Viscosity measuring tube 140 is, in the exemplary embodiment, a 0.496 inch inside diameter tube with pressure taps connected to the solenoid operated valves 140a, 140b, and 140c. A shear stress measurement is made automatically by opening two out of the three solenoid operated valves 140a-140c, thereby measuring the pressure drop across a short length of tube, such as between the valves 140c and 140b, or across a longer length of tube between valves 140c and 140a. Viscosity is calculated from the shear stress/shear rate relationship.

Similarly, viscosity measuring tube 141 is a 0.402 inch inside diameter tube with taps accessed by solenoid valves 141a-141c. Viscosity measuring tube 142 is a 0.311 inch inside diameter tube with three taps accessed by solenoid operated valves 142a-142c.

Viscosity measuring tubes 143 and 144 are annular tubes. Tube 143 has an outer tube with an inside diameter of 1.66 inches. It contains an inner tube with an outside diameter of 1½ inches. Tube 144 has an outer tube with an inside diameter of 0.62 inches and an inner tube with an outside diameter of 0.25 inches. Again, pressure is measured along a length between taps which are selected by solenoid operated valves. In this case, measurements are made in the annular space between the inner and outer tubes.

Annular viscosity measuring tubes 142 and 143 are provided with diametrically opposed pressure taps. If the inner tube is displaced, this may result in an erroneous pressure reading from a single tap. However, by using diametrically opposed taps, the pressure difference caused by displacement of the inner tube averages out.

Figure 7:
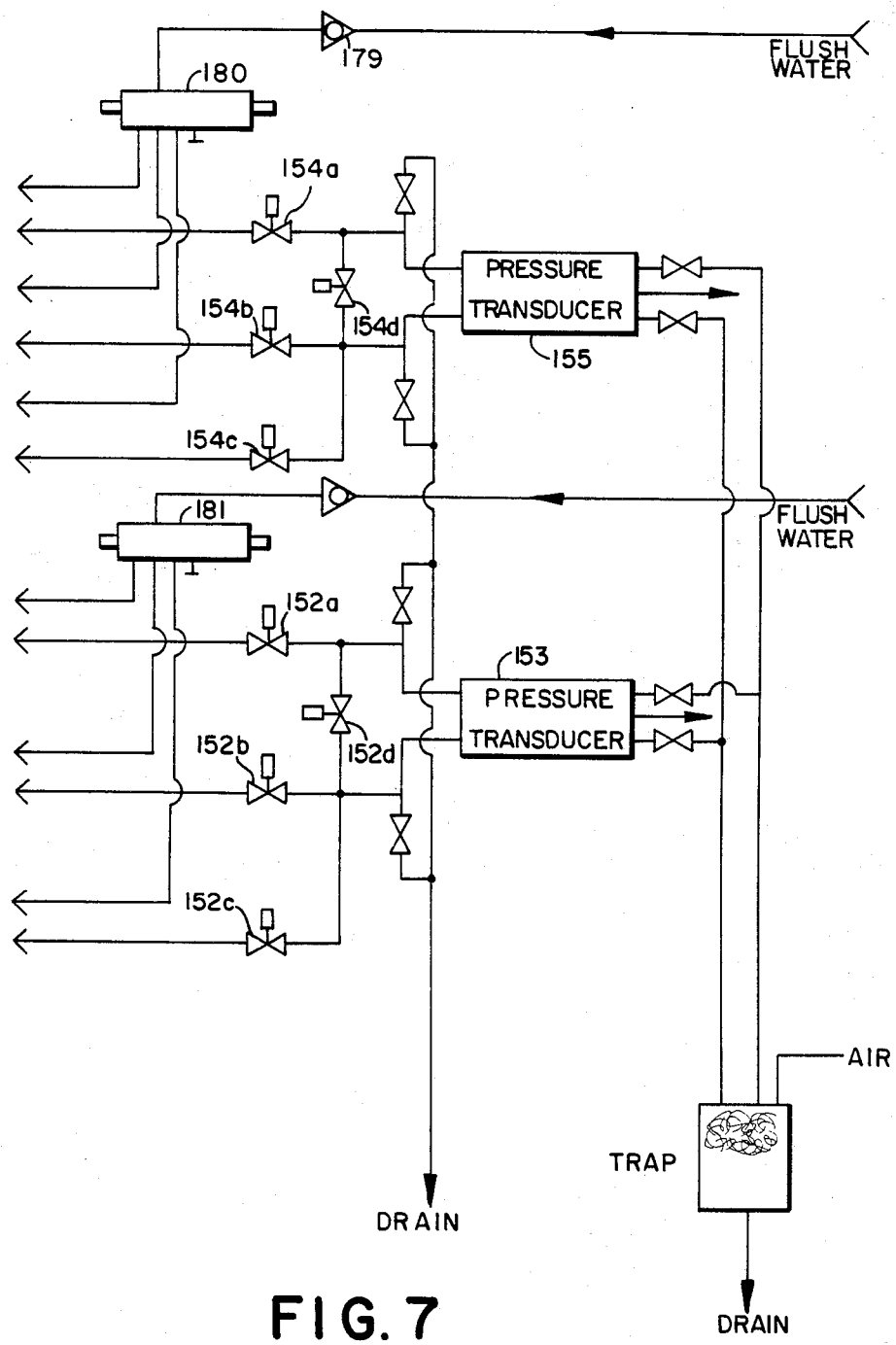

FIG. 7 shows the valving and manifolds for the viscosity measuring tubes 142 and 144 (FIG. 6). The valving and manifolds for the other three viscosity measuring tubes are similar. Referring first to the viscosity measuring tube 142, the pressure taps are connected through solenoid actuated valves 142a–c (FIG. 6) and 152a–d (FIG. 7) to the pressure transducer 153. Depending upon the actuation of these valves by the programmable controller, the pressure drop between two out of the three taps will be measured by the pressure transducer 153. Similarly, the three pressure taps on annular viscosity measuring tube 144 are connected through the solenoid operating valves 154a–d to the pressure transducer 155 which measures the pressure drop across the selected pressure taps of the viscosity measuring tube 144.

Referring to FIG. 8, the measuring section also includes a gamma source densitometer 160 that measures the density of the drilling mud. Flow meter 162 has valving which can be used to divert flow through the flow meter up to a temperature of 350° F. Above 350° F., flow is through the valve 163. Above 350° F. the tachometer 94a (FIG. 4) on the pump 94 is used to indicate flow through the system. Since pump heads 91–93 are positive displacement pumps, each stroke pumps a precise volume of drilling mud through the system. Therefore, the tachometer output provides a reliable measurement of flow through the system.

The flow of drilling mud can be diverted through the sample cell 164 (FIG. 8) to collect a sample of drilling mud therein. Flow is then returned to the normal path and desired measurements can be made on the drilling mud in the sample cell.

Pump 165 supplies additives from the reservoir 166 to the system. For example, a caustic such as sodium hydroxide is injected into the flow stream to maintain a high pH. Line 167 is connected to the line 167 in FIG. 3 to complete the closed loop system.

FIG. 9 shows the fluid flush pump 170 which is used to periodically flush certain points in the system with clean water. The flush pump is more fully described and claimed in co-pending application Ser. No. 518,336, filed July 29, 1983 "FLUSHING APPARATUS FOR A DRILLING MUD TESTING SYSTEM". Pump 170 has a piston which is actuated by pressurized air supplied through regulator 171. Slide valves 172–174 control the flow of air to both sides of the piston to acutate it in strokes which pressurize flush water from reservoir 175 to a pressure of approximately 1500 psi. The pressurized water is supplied through valve 176 to the manifold 177 which distributes it to the various taps of the viscosity measuring tubes. For example, flush water is supplied through line 178 and through check valve 179 (FIG. 7) and line select valve 180 to the taps of the annular viscosity measuring tube 144 (FIG. 6).

FIG. 7 also shows the line select valve 181 for supplying flush water to the taps of viscosity measuring tube 142 (FIG. 6). Similar flushing is provided for the other viscosity measuring tubes.

FIGS. 10 and 11 show the accumulator in more detail. The vessel body 110 holds a volume of drilling mud. A removable head 111 is secured to the vessel body 110 by the locking ring 112. Locking ring 112 engages the vessel body 110 at the threads 113.

Piston 81 is mounted on push rod 114 which moves through bearing surface 115 in the top of head 111. Wiper seals 116 engage the push rod 114. Pressurized nitrogen is supplied through line 117 to the top of the cylinder head 111 where it is applied to the top of the piston. The bottom of the piston 81 engages the drilling mud to pressurize it.

Compression seal 120 seals the connection between cylinder head 111 and the vessel body 110. All of the seals are in a position which are not normally contacted by the mud. Even if the vessel body 110 is filled with mud to a level where the seal 118 is in contact with the mud, there is no engagement of the piston with the seal in the mud so as to cause wear on the seals.

The head 111 is a heavy steel member adapted to withstand considerable pressure. In order to provide easy removal and replacement of the heavy head, a counter-balanced handle is provided. The counter-balance weight 122 is a cylinder which is filled with lead. It is connected by bars 123 and 124 (FIG. 11) to the handle 125. In order to remove the head from the accumulator, the locking ring 112 is disengaged from the threads of the vessel body by turning the ring with a bar inserted into one of the holes 126 or 127. After the threads have been disengaged, the head can be lifted from the vessel body by handle 125 with the weight of the head being counter-balanced by weight 122. The lifting bars 123 and 124 are pivoted about 128 (GIG. 11). With the head removed, the piston and seals can be inspected for wear. In order to fully extend the piston for inspection air is supplied through switching valve 129 to the top of the piston. In order to retract the piston, high pressure air is supplied through the switching valve 129 to the air line 130 which applies air to the side of the piston. This retracts the piston.

Valve 129 has two inputs, pressurized air and nitrogen. It switches them to the two outputs, one at the side of the piston at the end of tube 130, and the other at the top of the cylinder head at the end of tube 117. Switching valve 129 also connects the output to two vents.

Pressurized nitrogen is supplied to the valve through conduit 131 and pressurized air is supplied through conduit 132.

While a particular embodiment of the invention has been shown and described, various modifications are within the true spirit and scope of the invention. The appended claims are, therefore, intended to cover all such modifications.

What is claimed is:

1. A system for testing drilling mud comprising:
measuring means for testing the parameters of said drilling mud;
an accumulator for pressurizing said drilling mud;
means for pumping pressurized drilling mud through a closed recirculating path through said measuring means;
means for mixing and aging drilling mud to prepare drilling mud for testing; and
means for selectively supplying prepared drilling mud from said last named means to said accumulator to introduce drilling mud into the closed recirculating path of said system.

2. The system recited in claim 1 wherein said accumulator comprises:
a vessel holding a volume of drilling mud;
a piston having one side engaging said volume of drilling mud;
a source of pressurized air applied to the other side of said piston to pressurize said mud; and
a removable head for said vessel with seals for maintaining pressure in said vessel when said head is in place.

3. The system recited in claim 2 further comprising:
means for counter-balancing said removable head so that it can be easily positioned.

4. The system recited in claim 2 wherein said seals positioned on said vessel are out of contact with said drilling mud in said vessel.

5. The system recited in claim 2 wherein said seals include a threaded flange which cannot be opened when there is pressure in said vessel.

6. The system recited in claim 2 further comprising:
means for selectively applying pressurized air to both sides of said piston to extend it and to retract it for inspection and maintenance when said head is removed.

* * * * *